United States Patent
Govari et al.

(10) Patent No.: US 7,590,441 B2
(45) Date of Patent: Sep. 15, 2009

(54) INVASIVE MEDICAL DEVICE WITH POSITION SENSING AND DISPLAY

(75) Inventors: Assaf Govari, Haifa (IL); Yitzhack Schwartz, Haifa (IL)

(73) Assignee: Biosense, Inc., New Brunswick, NJ (US)

( * ) Notice: Subject to any disclaimer, the term of this patent is extended or adjusted under 35 U.S.C. 154(b) by 910 days.

(21) Appl. No.: 10/173,339

(22) Filed: Jun. 17, 2002

(65) Prior Publication Data

US 2003/0004411 A1  Jan. 2, 2003

Related U.S. Application Data

(63) Continuation-in-part of application No. 10/029,595, filed on Dec. 21, 2001, which is a continuation-in-part of application No. 09/265,715, filed on Mar. 11, 1999.

(51) Int. Cl.
*A61B 5/05* (2006.01)
(52) U.S. Cl. .................. 600/424; 600/407; 600/423; 600/437; 600/447
(58) Field of Classification Search .......... 600/309, 600/437, 562, 300, 424, 407, 423, 447; 606/1, 606/32
See application file for complete search history.

(56) References Cited

U.S. PATENT DOCUMENTS

| | | | |
|---|---|---|---|
| 3,644,825 A | 2/1972 | Davis, Jr. et al. ............ 324/41 |
| 3,713,133 A | 1/1973 | Nathans ...................... 340/280 |
| 3,868,565 A | 2/1975 | Kuipers ..................... 324/34 R |
| 4,017,858 A | 4/1977 | Kuipers .................... 343/100 R |
| 4,054,881 A | 10/1977 | Raab ....................... 343/112 R |
| 4,173,228 A | 11/1979 | Van Steenwyk et al. | |
| 4,317,078 A | 2/1982 | Weed et al. ................. 324/208 |
| 4,407,296 A | 10/1983 | Anderson | |
| 4,485,813 A | 12/1984 | Anderson et al. | |
| 4,560,930 A | 12/1985 | Kouno ....................... 324/207 |

(Continued)

FOREIGN PATENT DOCUMENTS

DE 30 11 671 A1 10/1981

(Continued)

OTHER PUBLICATIONS

U.S. Appl. No. 10/029,595, Biosense, Inc.

(Continued)

*Primary Examiner*—Brian Casler
*Assistant Examiner*—Baisakhi Roy
(74) *Attorney, Agent, or Firm*—Louis J. Capezzuto

(57) ABSTRACT

Apparatus for performing a medical procedure on a tissue within a body of a subject includes a wireless tag configured to be fixed to the tissue and adapted to emit radiation, thereby causing first signals to be generated indicative of a location of the tag in the body. An invasive medical tool includes a probe, which is adapted to penetrate into the body so as to reach the tissue. A handle is fixed proximally to the probe, for manipulation by an operator of the tool. A display, mounted on the handle, presents a visual indication to the operator of an orientation of the probe relative to the tag. A processing unit processes the first signals so as to determine coordinates of the tag relative to the probe, and drives the display responsive to the coordinates.

24 Claims, 9 Drawing Sheets

U.S. PATENT DOCUMENTS

| | | | |
|---|---|---|---|
| 4,613,866 A | 9/1986 | Blood | 343/448 |
| 4,642,786 A | 2/1987 | Hansen | 364/559 |
| 4,651,436 A | 3/1987 | Gaal | 33/533 |
| 4,710,708 A | 12/1987 | Rorden et al. | 324/207 |
| 4,807,202 A | 2/1989 | Cherri et al. | 367/129 |
| 4,815,469 A | 3/1989 | Cohen et al. | |
| 4,846,191 A | 7/1989 | Brockway et al. | |
| 4,849,692 A | 7/1989 | Blood | 324/208 |
| 4,905,698 A | 3/1990 | Strohl, Jr. et al. | 128/653 R |
| 4,917,095 A | 4/1990 | Fry et al. | 128/660.03 |
| 4,945,305 A | 7/1990 | Blood | 324/207.17 |
| 4,967,755 A | 11/1990 | Pondorf et al. | |
| 5,002,137 A | 3/1991 | Dickinson et al. | 175/19 |
| 5,042,486 A | 8/1991 | Pfeiler et al. | 128/653 R |
| 5,057,095 A | 10/1991 | Fabian | |
| 5,068,608 A | 11/1991 | Clark, Jr. | 324/220 |
| 5,078,144 A | 1/1992 | Sekino et al. | 128/660.03 |
| 5,099,845 A | 3/1992 | Besz et al. | 128/653.1 |
| 5,172,056 A | 12/1992 | Voisin | 324/207.17 |
| 5,201,715 A | 4/1993 | Masters | |
| 5,211,165 A | 5/1993 | Dumoulin et al. | 128/653.1 |
| 5,215,680 A | 6/1993 | D'Arrigo | 252/307 |
| 5,251,635 A | 10/1993 | Dumoulin et al. | 128/653.1 |
| 5,253,647 A | 10/1993 | Takahashi et al. | 128/653.1 |
| 5,255,680 A | 10/1993 | Darrow et al. | 128/653.1 |
| 5,265,610 A | 11/1993 | Darrow et al. | 128/653.1 |
| 5,269,289 A | 12/1993 | Takehana et al. | 128/4 |
| 5,273,025 A | 12/1993 | Sakiyama et al. | 128/6 |
| 5,275,166 A | 1/1994 | Vaitekunas et al. | 128/660.03 |
| 5,295,486 A | 3/1994 | Wollschlager et al. | 128/661.01 |
| 5,309,913 A | 5/1994 | Kormos et al. | 128/653.1 |
| 5,325,873 A | 7/1994 | Hirschi et al. | 128/899 |
| 5,330,520 A | 7/1994 | Maddison et al. | |
| 5,353,354 A | 10/1994 | Keller et al. | |
| 5,353,800 A | 10/1994 | Pohndorf et al. | |
| 5,375,596 A | 12/1994 | Twiss et al. | 128/653.1 |
| 5,377,678 A | 1/1995 | Dumoulin et al. | 128/653.1 |
| 5,383,874 A | 1/1995 | Jackson et al. | 606/1 |
| 5,391,199 A | 2/1995 | Ben-Haim et al. | 607/122 |
| 5,404,877 A | 4/1995 | Nolan et al. | |
| 5,412,619 A | 5/1995 | Bauer | 367/128 |
| 5,425,367 A | 6/1995 | Shapiro et al. | 128/653.1 |
| 5,425,382 A | 6/1995 | Golden et al. | 128/899 |
| 5,429,132 A | 7/1995 | Guy et al. | 128/653.1 |
| 5,437,277 A | 8/1995 | Dumoulin et al. | 128/653.1 |
| 5,443,489 A | 8/1995 | Ben-Haim | 607/115 |
| 5,453,687 A | 9/1995 | Zierdt et al. | 324/207.17 |
| 5,456,718 A | 10/1995 | Szymaitis | |
| 5,471,988 A | 12/1995 | Fujio et al. | 128/660.03 |
| 5,513,636 A | 5/1996 | Palti | |
| 5,522,869 A | 6/1996 | Burdette et al. | 607/97 |
| 5,549,638 A | 8/1996 | Burdette | 607/97 |
| 5,558,091 A | 9/1996 | Acker et al. | 128/653.1 |
| 5,558,092 A | 9/1996 | Unger et al. | 128/660.03 |
| 5,566,676 A | 10/1996 | Rosenfeldt et al. | |
| 5,577,502 A | 11/1996 | Darrow et al. | 128/653.1 |
| 5,617,857 A | 4/1997 | Chader et al. | 128/653.1 |
| 5,622,169 A | 4/1997 | Golden et al. | 128/653.1 |
| 5,636,644 A | 6/1997 | Hart et al. | |
| 5,645,065 A | 7/1997 | Kay et al. | |
| 5,682,886 A | 11/1997 | Delp et al. | 128/653.1 |
| 5,689,576 A | 11/1997 | Schneider et al. | |
| 5,690,113 A | 11/1997 | Sliwa, Jr. et al. | |
| 5,694,945 A | 12/1997 | Ben-Haim | 128/736 |
| 5,697,377 A | 12/1997 | Wittkampf | 128/696 |
| 5,715,822 A | 2/1998 | Watkins et al. | 128/653.5 |
| 5,727,552 A | 3/1998 | Ryan | |
| 5,729,129 A | 3/1998 | Acker et al. | 324/207.12 |
| 5,743,267 A | 4/1998 | Nikolic et al. | |
| 5,752,513 A | 5/1998 | Acker et al. | 128/653.1 |
| 5,762,066 A | 6/1998 | Law et al. | |
| 5,762,609 A * | 6/1998 | Benaron et al. | 600/473 |
| 5,769,843 A | 6/1998 | Abela et al. | 606/10 |
| 5,797,849 A | 8/1998 | Vesely et al. | 600/461 |
| 5,817,022 A | 10/1998 | Vesely | |
| 5,868,673 A * | 2/1999 | Vesely | 600/407 |
| 5,913,820 A | 6/1999 | Bladen et al. | |
| 5,928,137 A * | 7/1999 | Green | 600/160 |
| 5,964,709 A | 10/1999 | Chiang et al. | |
| 5,999,857 A | 12/1999 | Weijand et al. | |
| 6,021,352 A | 2/2000 | Christopherson et al. | |
| 6,026,818 A | 2/2000 | Blair et al. | |
| 6,053,873 A | 4/2000 | Govari et al. | |
| 6,073,043 A | 6/2000 | Schneider | |
| 6,076,007 A | 6/2000 | England et al. | |
| 6,140,740 A | 10/2000 | Porat et al. | |
| 6,141,293 A | 10/2000 | Amorai-Moriya et al. | |
| 6,159,156 A | 12/2000 | Van Bockel | |
| 6,161,032 A | 12/2000 | Acker | |
| 6,172,499 B1 | 1/2001 | Ashe | |
| 6,198,963 B1 | 3/2001 | Haim et al. | |
| 6,206,835 B1 | 3/2001 | Spillman, Jr. et al. | |
| 6,223,066 B1 | 4/2001 | Govari | |
| 6,226,547 B1 | 5/2001 | Lockhart et al. | |
| 6,237,398 B1 | 5/2001 | Porat et al. | |
| 6,239,724 B1 | 5/2001 | Doron et al. | |
| 6,270,458 B1 | 8/2001 | Barnea | |
| 6,305,381 B1 | 10/2001 | Weijand et al. | |
| 6,332,089 B1 | 12/2001 | Acker et al. | |
| 6,347,241 B2 * | 2/2002 | Burbank et al. | 600/431 |
| 6,373,240 B1 | 4/2002 | Govari | |
| 6,380,732 B1 | 4/2002 | Gilboa | |
| 6,490,474 B1 | 12/2002 | Willis et al. | |
| 6,638,231 B2 | 10/2003 | Govari et al. | |
| 6,788,967 B2 | 9/2004 | Ben-Haim et al. | |
| 6,875,179 B2 * | 4/2005 | Ferguson et al. | 600/461 |
| 7,160,258 B2 | 1/2007 | Imran et al. | |
| 7,174,201 B2 * | 2/2007 | Govari et al. | 600/424 |
| 2001/0018594 A1 | 8/2001 | Krag | |
| 2001/0051766 A1 * | 12/2001 | Gazdzinski | 600/309 |
| 2002/0107445 A1 * | 8/2002 | Govari | 600/437 |
| 2003/0004407 A1 * | 1/2003 | Carroll et al. | 600/407 |
| 2003/0023161 A1 | 1/2003 | Govari et al. | |
| 2003/0120150 A1 * | 6/2003 | Govari | 600/424 |
| 2004/0015075 A1 * | 1/2004 | Kimchy et al. | 600/424 |
| 2004/0015079 A1 * | 1/2004 | Berger et al. | 600/437 |

FOREIGN PATENT DOCUMENTS

| | | |
|---|---|---|
| DE | 100 03 338 A | 11/2000 |
| EP | 0 021 451 A1 | 7/1981 |
| EP | 0 053 976 A2 | 6/1982 |
| EP | 0 646 365 A1 | 4/1995 |
| EP | 0 897 690 A1 | 2/1999 |
| EP | 1 004 267 A2 | 5/2000 |
| EP | 1 034 738 A | 9/2000 |
| JP | 60-70324 A | 4/1985 |
| JP | H08-015489 B2 | 2/1996 |
| JP | 08 313622 | 11/1996 |
| WO | WO 83 02053 A | 6/1983 |
| WO | WO 83/03348 A1 | 10/1983 |
| WO | WO 92/03090 | 3/1992 |
| WO | WO 94/04938 | 3/1994 |
| WO | WO 94/23647 | 10/1994 |
| WO | WO 96/05768 | 2/1996 |
| WO | WO 96/05768 A1 | 2/1996 |
| WO | WO 96/41119 | 12/1996 |
| WO | WO 97/29678 | 8/1997 |
| WO | WO 97/29701 | 8/1997 |
| WO | WO 97/29709 | 8/1997 |
| WO | WO 97/29710 | 8/1997 |
| WO | WO 97/32179 | 9/1997 |
| WO | WO 97/33513 A1 | 9/1997 |
| WO | WO 98/11840 | 3/1998 |

| | | |
|---|---|---|
| WO | WO 98/36236 | 8/1998 |
| WO | WO 99 27837 A | 6/1999 |
| WO | WO 99/34453 A1 | 7/1999 |
| WO | WO 99/34453 AL | 7/1999 |
| WO | WO 99/34731 A1 | 7/1999 |
| WO | WO 99 51143 A | 10/1999 |
| WO | WO 00/16686 A2 | 3/2000 |
| WO | WO 00/16686 A3 | 3/2000 |
| WO | WO 00/32092 A1 | 6/2000 |
| WO | WO 01/36014 A2 | 5/2001 |
| WO | WO 01 64109 A | 9/2001 |
| WO | WO 02 39917 A | 5/2002 |

OTHER PUBLICATIONS

U.S. Appl. No. 10/029,473, Biosense, Inc.

Weir, R.F. et al.: "A Portable, Real-Time, Clinical Gait Velocity Analysis System", IEEE Transactions on Rehabilitation Engineering, US, NY, vol. 5 No. 4 p. 310-320, Dec. 1997.

EPO Search Report dated Oct. 14, 2003 for EPO Application No. EP 03 25 3786.

EPO Search Report dated Oct. 13, 2003 for EPO Application No. EP 03 25 3784.

EPO Search Report dated Oct. 13, 2003 for EPO Application No. EP 03 25 3785.

EPO Search Report dated Dec. 4, 2003 for EPO Application No. EP 02 25 8960.

Dargie, Henry J. "Diagnosis and Management of Heart Failure", BMJ 1994;308:321-8.

Stevenson, LW & Perloff, JK "The Limited Reliability of Physical Signs for Estimating Hemodynamics in Chronic Heart Failure", JAMA 1989;261, No. 6:884-888.

Chakko S et al. "Clinical, Radiographic, and Hemodynamic Correlations in Chronic Congestive Heart Failure: Conflicting Results May Lead to Inappropriate Care", AJM 1991;90:353-359.

Stevenson LW "Tailored Therapy Before Transplantation for Treatment of Advanced Heart Failure: Effective Use of Vasodilators and Diuretics", J Heart Lung Transplant 1991;10:468-76.

Stevenson LW et al. "Poor Survival of Patients with Idopathic Cardiomyopathy Considered Too Well for Transplantation", AJM 1987;83:871-876.

Steinhaus David M et al. "Initial Experience with an Implantable Hemodynamic Monitor", Circulation 1996;93No. 4:745-752.

Ohlsson A et al. "Continuous Ambulatory Haemodynamic Monitoring with an Implantable System", European Heart Journal 1998;19:174-184.

* cited by examiner

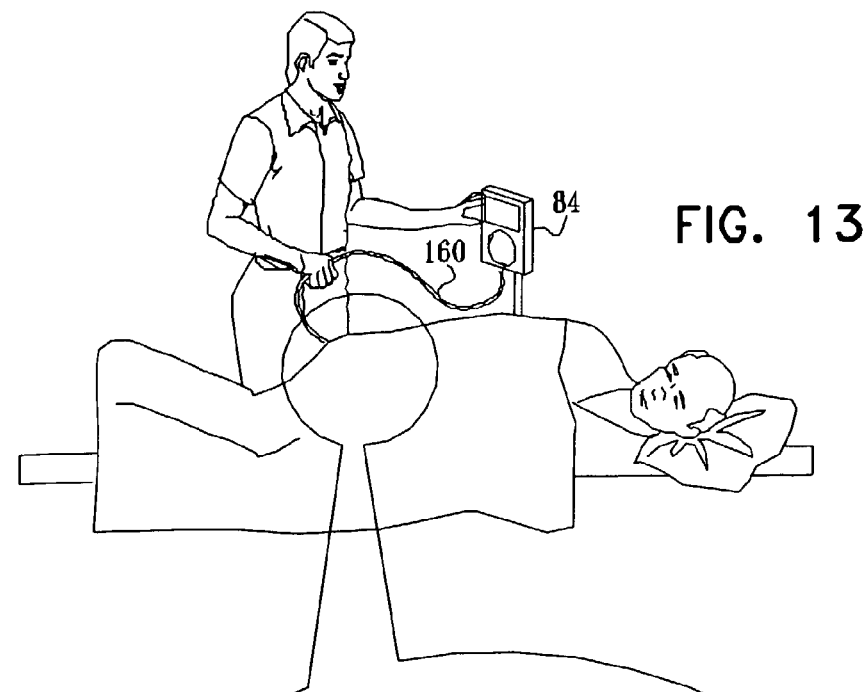
FIG. 13
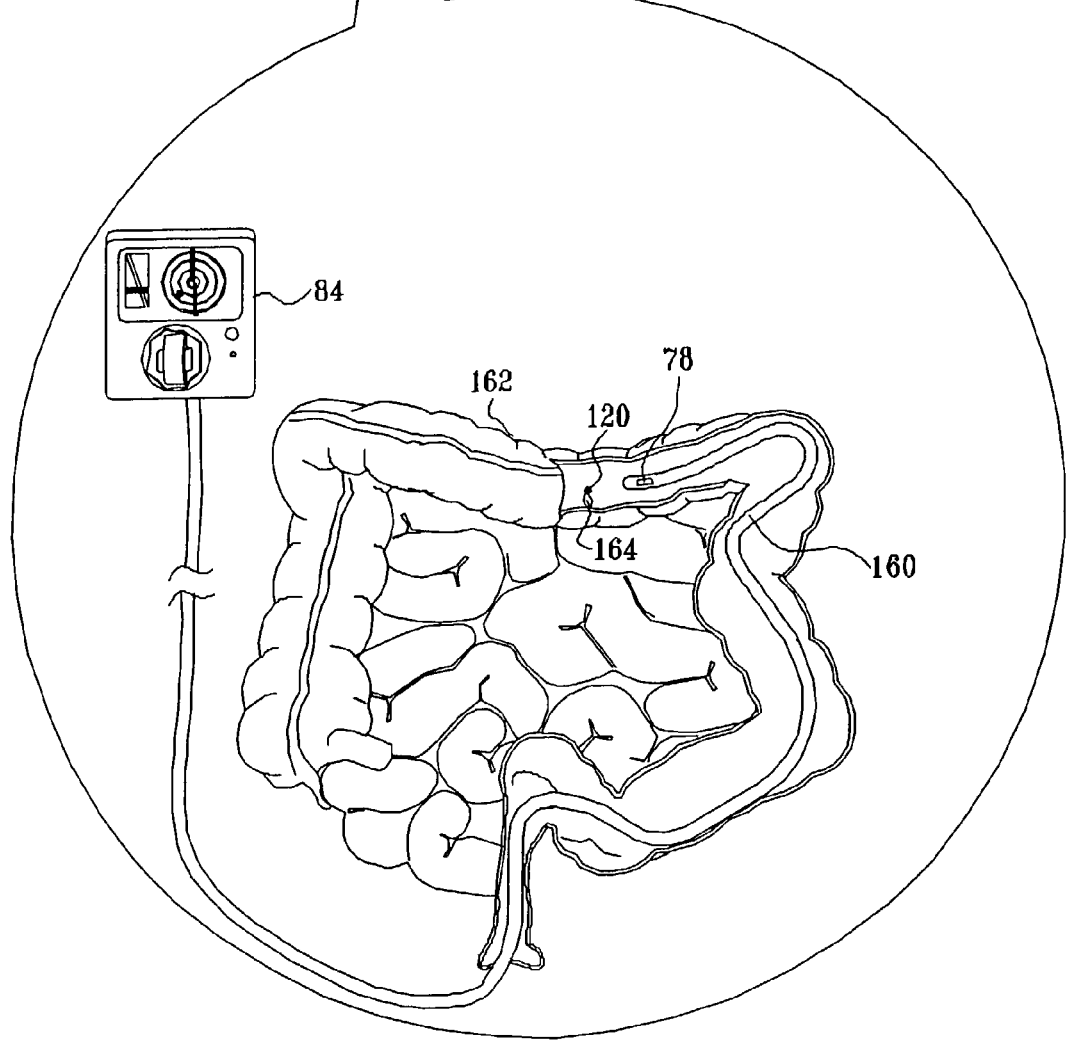

INVASIVE MEDICAL DEVICE WITH POSITION SENSING AND DISPLAY

CROSS-REFERENCE TO RELATED APPLICATIONS

This application is a continuation-in-part of U.S. patent application Ser. No. 10/029,595, filed Dec. 21, 2001, which is a continuation-in-part of U.S. patent application Ser. No. 09/265,715, filed Mar. 11, 1999. This application is also related to two other U.S. patent applications, filed on even date, entitled "Guidance of Invasive Medical Procedures Using Implantable Tags," and "Position Sensing System with Integral Location Pad and Position Display." All these related applications are incorporated herein by reference.

FIELD OF THE INVENTION

The present invention relates generally to systems for determining the position of an object inside a human body, and specifically to the use of such systems in guiding tools and other devices used in medical procedures.

BACKGROUND OF THE INVENTION

The use of implanted markers or clips for surgical guidance is known in the art. For example, upon identifying a suspicious lesion in the breast, a radiologist may mark the location by inserting a simple radio-opaque wire at the location of the lesion while viewing an image of the breast under mammography. When a biopsy is subsequently performed, the surgeon follows the wire to find the exact location of the lesion, so as to be certain of removing tissue from the correct area of the breast. Radiologists currently use this sort of location marking for approximately 40% of all breast biopsies. This careful approach significantly reduces the occurrence of false negative biopsy findings and increases the overall diagnostic accuracy of the procedure.

Despite the proven usefulness of such simple biopsy markers, it would be preferable for the surgeon to be able to choose a pathway to the biopsy site independently, rather than having to follow the wire inserted by the radiologist. Furthermore, wire-based markers are not appropriate to other invasive procedures, such as lung biopsies, or to applications in which a marker must be left in the body for extended periods. It has therefore been suggested to use a wireless emitter, or "tag," to mark target locations in the body for surgery and therapy. Such a tag contains no internal power source, but is rather actuated by an external energy field, typically applied from outside the body. The tag then emits ultrasonic or electromagnetic energy, which is detected by antennas or other sensors outside the body. The detected signals may be used to determine position coordinates of the tag. Passive ultrasonic reflectors are one simple example of such tags. Other passive tags receive and re-emit electromagnetic radiation, typically with a frequency and/or phase shift. Hybrid tags, combining ultrasonic and electromagnetic interactions, are also known in the art.

For example, U.S. Pat. No. 6,026,818, to Blair et al., whose disclosure is incorporated herein by reference, describes a method and device for the detection of unwanted objects in surgical sites, based on a medically inert detection tag which is affixed to objects such as medical sponges or other items used in body cavities during surgery. The detection tag contains a single signal emitter, such as a miniature ferrite rod and coil and capacitor element embedded therein. Alternatively, the tag includes a flexible thread composed of a single loop wire and capacitor element. A detection device is utilized to locate the tag by pulsed emission of a wide-band transmission signal. The tag resonates with a radiated signal, in response to the wide-band transmission, at its own single non-predetermined frequency, within the wide-band range. The return signals build up in intensity at a single (though not pre-defined) detectable frequency over ambient noise, so as to provide recognizable detection signals.

U.S. Pat. No. 5,325,873, to Hirschi et al., whose disclosure is incorporated herein by reference, describes a system to verify the location of a tube or other object inserted into the body. It incorporates a resonant electrical circuit attached to the object which resonates upon stimulation by a hand-held RF transmitter/receiver external to the body. The electromagnetic field generated due to resonance of the circuit is detected by the hand-held device, which subsequently turns on a series of LEDs to indicate to the user the direction to the target. An additional visual display indicates when the transmitter/receiver is directly above the object.

U.S. Pat. No. 6,239,724, to Doron et al., whose disclosure is incorporated herein by reference, describes a telemetry system for providing spatial positioning information from within a patient's body. The system includes an implantable telemetry unit having (a) a first transducer, for converting a power signal received from outside the body into electrical power for powering the telemetry unit; (b) a second transducer, for receiving a positioning field signal that is received from outside the body; and (c) a third transducer, for transmitting a locating signal to a site outside the body, in response to the positioning field signal.

U.S. Pat. No. 6,332,089, to Acker et al., whose disclosure is incorporated herein by reference, describes a medical probe such as a catheter, which is guided within the body of a patient by determining the relative positions of the probe relative to another probe, for example by transmitting nonionizing radiation to or from field transducers mounted on both probes. In one embodiment, a site probe is secured to a lesion within the body, and an instrument probe for treating the lesion may be guided to the lesion by monitoring relative positions of the probes. Two or more probes may be coordinated with one another to perform a medical procedure.

Passive sensors and transponders, fixed to implanted devices, can also be used for conveying other diagnostic information to receivers outside the body. For example, U.S. Pat. No. 6,053,873, to Govari et al., whose disclosure is incorporated herein by reference, describes a stent adapted for measuring a fluid flow in the body of a subject. The stent contains a coil, which receives energy from an electromagnetic field irradiating the body so as to power a transmitter for transmitting a pressure-dependent signal to a receiver outside the body. In one embodiment, the transmitter is based on a tunnel diode oscillator circuit, suitably biased so as to operate in a negative resistance regime, as is known in the art.

As another example, U.S. Pat. No. 6,206,835 to Spillman et al., whose disclosure is incorporated herein by reference, describes an implant device that includes an integral, electrically-passive sensing circuit, communicating with an external interrogation circuit. The sensing circuit includes an inductive element and has a has a frequency-dependent variable impedance loading effect on the interrogation circuit, varying in relation to the sensed parameter.

SUMMARY OF THE INVENTION

It is an object of some aspects of the present invention to provide methods and systems for guidance of medical procedures.

In preferred embodiments of the present invention, a wireless tag is implanted in a patient's body to mark the location of a planned diagnostic or therapeutic procedure. During the procedure, the region of the body under treatment is irradiated with electromagnetic radiation (typically radio frequency—RF—radiation) or ultrasonic radiation, causing the tag to return energy indicative of its location. The energy returned from the tag is detected by a receiver in order to determine the location and orientation of a therapeutic or diagnostic device, such as a surgical probe, relative to the tag. The radiation source and the receiver for detecting the returned energy may be integrated into the therapeutic or diagnostic device, or they may alternatively be contained in one or more separate units. In the latter case, when the receiver is separate from the therapeutic or diagnostic device, the receiver is preferably also capable of determining the position and orientation of the device.

The location and orientation of the therapeutic or diagnostic device relative to the tag within the body are shown on a display, for use by the treating physician in guiding the device to the appropriate location. In some preferred embodiments of the present invention, the display is integrated in a single unit with the therapeutic or diagnostic device that must be guided, for example, on a handle of the device. The operator is thus able to guide the device while looking only at the tool and the region under treatment, without having to look away toward a separate display as in systems known in the art.

Various different types of wireless tags may be used for the purposes of the present invention. Preferably, the tag is passive, in the sense that it contains no internal energy source, but rather derives all the energy that it needs to operate from the applied electromagnetic or ultrasonic radiation. Exemplary passive tags are described in the above-mentioned U.S. patent application Ser. No. 10/029,595 and in U.S. patent application Ser. No. 10/029,473, filed Dec. 21, 2001, which is assigned to the assignee of the present patent application and whose disclosure is likewise incorporated herein by reference. Other types of tags, as are known in the art, may also be used.

Systems and methods in accordance with embodiments of the present invention present invention are particularly useful in guiding biopsies and other invasive procedures performed on soft tissues, such as the breasts, lungs and gastrointestinal tract. Implantation of a passive tag can be used both to provide initial guidance to the location of a suspected lesion and to provide further guidance to return to the same location in subsequent treatment and follow-up. Such guidance systems may also be used in non-invasive therapies, such as focused radiotherapy and ultrasound, to focus high-intensity radiation from a source outside the body onto the precise location of a lesion. Other applications will be apparent to those skilled in the art.

There is therefore provided, in accordance with a preferred embodiment of the present invention, apparatus for performing a medical procedure on a tissue within a body of a subject, including:

a wireless tag configured to be fixed to the tissue and adapted to emit radiation, thereby causing first signals to be generated indicative of a location of the tag in the body;

an invasive medical tool, including:

a probe, which is adapted to penetrate into the body so as to reach the tissue;

a handle, fixed proximally to the probe, and adapted to be manipulated by an operator of the tool; and a display, mounted on the handle, and adapted to present a visual indication to the operator of an orientation of the probe relative to the tag; and a processing unit, coupled to process the first signals so as to determine coordinates of the tag relative to the probe, and to drive the display responsive to the coordinates.

Preferably, the invasive medical tool further includes a receiver, which is adapted to receive the radiation emitted by the wireless tag, and to generate the first signals responsive thereto for processing by the processing unit.

Further preferably, the invasive medical tool includes a tool position sensor, which is adapted to generate second signals indicative of the coordinates of the probe, and the processing unit is coupled to process the second signals together with the first signals so as to determine the coordinates of the tag relative to the probe. In a preferred embodiment, the apparatus includes one or more field generators, which are fixed in the external frame of reference and which are adapted to generate electromagnetic fields in a vicinity of the tissue, and the wireless tag and the tool position sensor include field sensors, in which electrical currents flow responsive to the electromagnetic fields, and wherein the first and second signals are indicative of the electrical currents flowing in the field sensors.

Preferably, the radiation emitted by the tag includes radio-frequency (RF) electromagnetic radiation. In a preferred embodiment, the apparatus includes one or more acoustic transmitters, which are adapted to transmit acoustic energy into the body in a vicinity of the tissue, and wherein the tag is adapted to receive and use the acoustic energy in generating the electromagnetic radiation.

Alternatively, the radiation emitted by the tag includes acoustic radiation.

Preferably, the display is adapted to present a further visual indication of a distance from the probe to the tag.

In a preferred embodiment, the invasive medical tool is adapted to perform a surgical procedure on the tissue. Additionally or alternatively, the invasive tool includes an endoscope.

There is also provided, in accordance with a preferred embodiment of the present invention, a method for performing a medical procedure on a tissue within a body of a subject, including:

fixing a wireless tag to the tissue;

actuating the tag to emit radiation, thereby causing first signals to be generated indicative of a location of the tag in the body;

introducing an invasive medical tool into the body by manipulating a handle of the tool;

processing the first signals so as to determine coordinates of the tag relative to the tool;

responsive to the coordinates, displaying a visual indication on the handle of the tool of an orientation of the tool relative to the tag; and advancing the tool into the body to the tissue by manipulating the handle while observing the visual indication so that the tool reaches the tissue.

The present invention will be more fully understood from the following detailed description of the preferred embodiments thereof, taken together with the drawings in which:

BRIEF DESCRIPTION OF THE DRAWINGS

FIG. 13 is a schematic, pictorial illustration of a system for guiding an endoscope to the location of a passive tag in the colon of a subject, in accordance with still another preferred embodiment of the present invention.

DETAILED DESCRIPTION OF PREFERRED EMBODIMENTS

Figure 1:
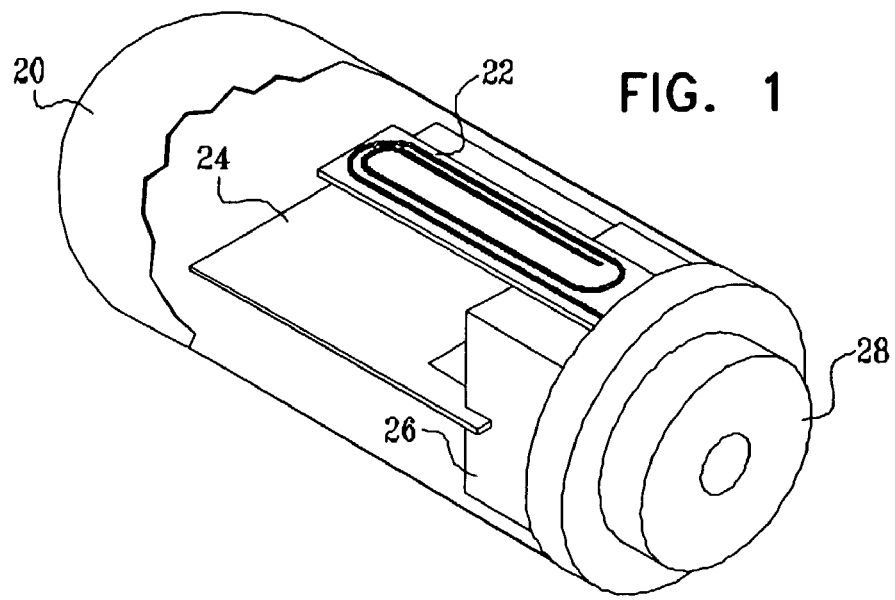
FIG. 1 is a schematic, pictorial illustration showing a partly-cutaway view of an implantable passive tag, in accordance with a preferred embodiment of the present invention.

FIG. 1 is a schematic, pictorial illustration that shows a partly-cutaway view of an implantable passive tag 20, in accordance with a preferred embodiment of the present invention. Tag 20 of the type shown and described here is also referred to herein as a "beacon." The tag comprises a RF antenna 22, typically having the form of a coil, which is coupled to a capacitor 24 and additional circuitry 26 to define a resonant circuit. The coil, capacitor and circuitry are contained in a sealed, biocompatible package 28, typically made of a plastic or other non-conducting material. In the embodiment pictured in FIG. 1, package 28 includes a base that can be grasped by a radiologist using a suitable inserter tool (not shown in the figures) to position tag 20 at a desired location in soft tissue of a patient.

Preferably, circuitry 26 comprises a tunnel diode (not shown), such as a 1n3712 diode, which is configured together with antenna 22 and capacitor 24 to form a tunnel diode oscillator circuit, as is known in the art. For example, the antenna may be formed by a small loop of 0.5 mm wire, and coupled to a 40 pF capacitor. Further details of the design of a tunnel diode oscillator circuit and its use in a wireless transponder are described in the above-mentioned U.S. Pat. No. 6,053,873. In brief, the oscillator circuit is excited by an externally-generated electromagnetic field at a first frequency (f1), which causes the oscillator circuit to radiate a response field at another frequency (f2). Tunnel diodes are particularly well suited for this purpose, because the characteristic I-V curve of a tunnel diode includes a portion in which the diode demonstrates "negative" resistance, i.e., as the voltage applied across the diode decreases, the current through the diode increases, causing oscillations to occur in the circuit. The oscillation frequency (f2) differs from the normal resonant frequency of the circuit because of the effective capacitance of the tunnel diode. Typically, frequency f2 differs from the excitation frequency f1 by about 10%-40%. For example, an excitation frequency f1 of 88 MHz may yield a response field having a frequency f2 of 120 MHz. The intensity and direction of the response field can be used to "home in" on the location of tag 20, as described below. Alternatively, other types of re-radiating oscillators may be used for this purpose, as well.

Figure 2:
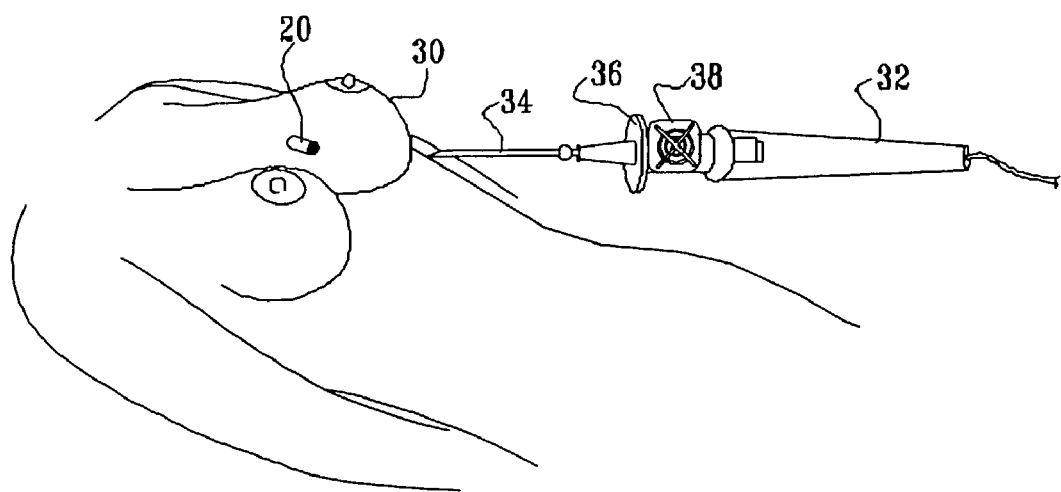
FIG. 2 is a schematic, pictorial illustration showing a surgical probe that is guided to the location of a passive tag in the breast of a subject using a display on the probe, in accordance with a preferred embodiment of the present invention.

FIG. 2 is a schematic, pictorial illustration showing implantation of tag 20 in a breast 30 of a patient, and its use in guiding a surgical tool 32, in accordance with a preferred embodiment of the present invention. Typically, tool 32 comprises a probe 34, which is used, for example, to cut and extract a biopsy sample from breast 30 at the location marked by tag 20. Tool 32 comprises an antenna assembly 36, which is coupled to excitation and detection circuitry, contained either within tool 32 or in a separate processing unit (not shown in this figure). Antenna assembly 36 is driven to radiate RF energy at or near the excitation frequency f1 of the circuitry in tag 20. This excitation energy causes the tag to radiate a response field at frequency f2, which is detected by the antenna assembly. Typically, antenna assembly 36 comprises two or more antennas (not shown), spaced around the longitudinal axis of probe 34. The difference between the respective field strengths sensed by the antennas at frequency f2 is indicative of the direction and magnitude of the misalignment of the probe axis relative to the location of tag 20. Based on the detected response fields, a display 38 on the handle of tool 32 guides the surgeon in directing probe 34 precisely to the location of tag 20. When the signals from the antennas are equal, the probe axis is aligned with the tag.

Figure 3:
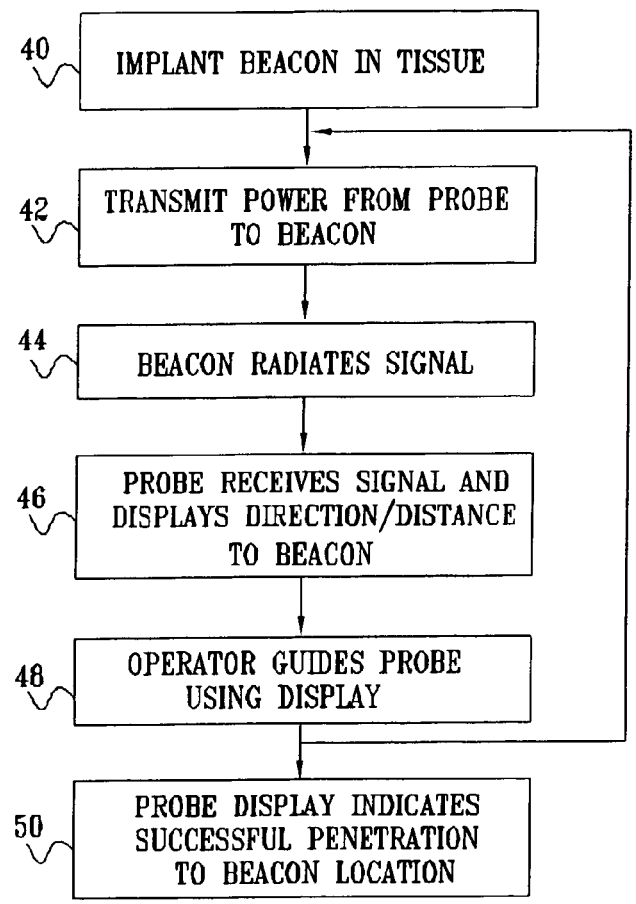
FIG. 3 is a flow chart that schematically illustrates a method for carrying out an invasive medical procedure on body tissue using a tag implanted in the tissue, in accordance with a preferred embodiment of the present invention.

FIG. 3 is a flow chart that schematically illustrates a method for performing a surgical procedure using tag 20 and tool 32, in accordance with a preferred embodiment of the present invention. The tag is initially implanted in breast 30 by a radiologist, at an implant step 40. This step is typically carried out while imaging the breast to determine the location of a suspicious lesion, so as to place tag 20 within or adjacent to the lesion. A surgeon then brings probe 34 into proximity with breast. Antenna assembly 36 transmits a RF field in the direction of probe 34, toward breast 30, at a power transmission step 42. As noted above, the transmitted field is at or near the excitation frequency of the oscillator circuit in tag 20. The oscillation thus engendered in the circuit causes it to radiate a response field, or beacon signal, at a beacon transmission step 44.

Antenna assembly 36 receives the beacon signal, at a beacon reception step 46, and the signal is processed to measure its strength and, optionally, its directional characteristics. These characteristics are used in driving display 38 to give the surgeon a visual indication of how probe 34 should be directed through the breast tissue in order to reach tag 20. In one embodiment, display 38 simply gives a signal strength indication, and the surgeon directs the probe so as to maximize the signal strength. In another embodiment, the response signal is processed to generate a directional signal, typically using multiple antennas in assembly 36, as described above. The antenna outputs are processed, using analog and/or digital differential processing circuitry, to drive a pointer or cursor on display 38, indicating the direction from probe 34 to tag 20. Optionally, tool 32 also provides an audible indication, such as a tone or sequence of tones, to cue the surgeon as to whether or not the probe is correctly directed to the target in breast 30.

The surgeon uses the information provided by display 38 to guide probe 34 toward tag 20, at a guidance step 48. Steps 42 through 48 are repeated continually until the distal tip of probe 34 reaches the location of tag 20, at a success step 50. Successful penetration by the probe tip to the tag location can be determined in a number of different ways. For example, an antenna or other sensor may be incorporated in the probe near its distal tip in order to signal when the probe contacts the tag. Alternatively, each of the multiple antennas in assembly 36 can be used to find a respective directional vector, pointing from the antenna to the tag location. The crossing point of these vectors indicates the location of the tag. It is thus determined that the probe tip has reached the tag location when the distance from antenna assembly 36 to the vector crossing point is equal to the known length of probe 34. At this point, display 38 preferably gives an indication of success, such as a change in color or audible signal. The surgeon can then complete the biopsy or other procedure that is warranted. Tag 20 may either be surgically removed as part of this procedure, or it may be left in place for future access.

Figure 4:
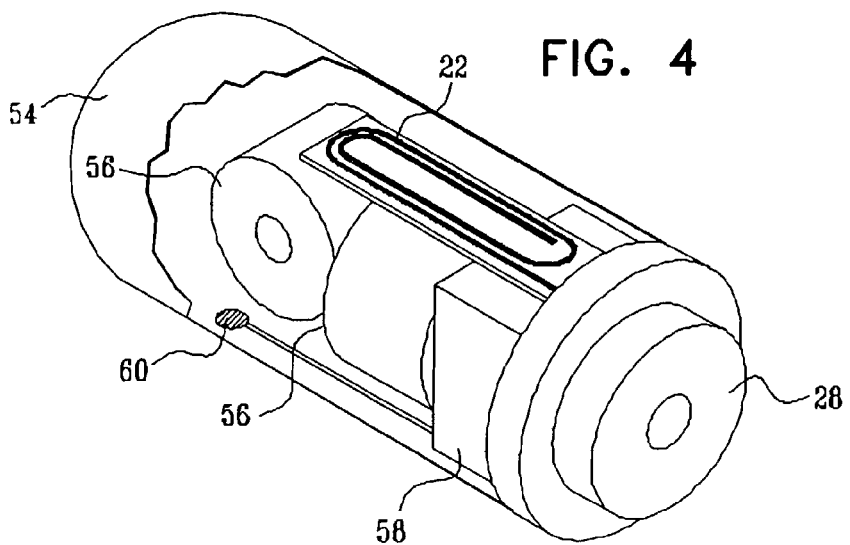
FIG. 4 is a schematic, pictorial illustration showing a partly-cutaway view of an implantable passive tag, in accordance with another preferred embodiment of the present invention.

FIG. 4 is a schematic, pictorial illustration that shows a partly-cutaway view of an implantable passive tag 54, in accordance with another preferred embodiment of the present invention. Tag 54 comprises, in addition to antenna 22, one or more position-sensing coils 56. Application of electromagnetic fields to coils 56 by external field generators causes currents to flow in these coils. The amplitudes of the currents can be used to determine the position and orientation coordinates of the coils relative to the field generators (as shown below in FIG. 6). Exemplary methods for determining position and orientation of an invasive device using coils such as these are described in U.S. Pat. No. 5,391,199, to Ben-Haim, and in U.S. patent application Ser. No. 08/793,371 filed May 14, 1997 (PCT Patent Publication WO 96/05768, to Ben-Haim et al.), whose disclosures are incorporated herein by reference. Three position-sensing coils 56 can be used to provide six-dimensional location and orientation coordinates of tag 54. For applications that do not require full, six-dimensional information, a single position-sensing coil is adequate.

Coils 56 are coupled to control circuitry 58, which senses the currents flowing in the coils for use in determining the coordinates of tag 54. Preferably, circuitry 58 generates signals in which the current magnitudes are encoded and causes these signals to be transmitted by antenna 22. The signals are decoded and processed by an external processing unit to determine the coordinates of the tag. Optionally, tag 54 may also comprise one or more additional sensors 60, which measure physiological parameters at the site of the tag in the body. Examples of such sensors include temperature sensors, pressure sensors, pH sensors, and other sensors for measuring physical and chemical properties of tissues with which tag 54 is in contact. Circuitry 58 encodes and transmits these sensor measurements, as well.

Figure 5:
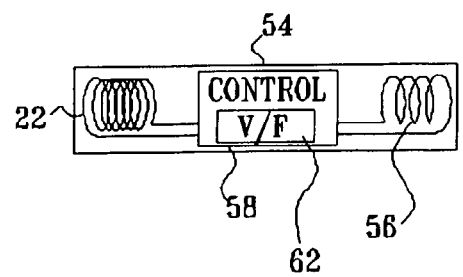
FIG. 5 is a schematic electrical diagram of a passive tag, in accordance with a preferred embodiment of the present invention.

FIG. 5 is an electrical schematic diagram showing circuit elements of tag 54, in accordance with a preferred embodiment of the present invention. Antenna 22 is preferably optimized to receive and transmit high-frequency signals, in the range above 1 MHz. Coil 56, on the other hand, is preferably designed for operation in the range of 1-3 kHz, at which the external field generators generate their electromagnetic fields. Alternatively, other frequency ranges may be used, as dictated by application requirements. According to this embodiment, tag 54 can typically be made about 2-5 mm in length and 2-3 mm in outer diameter. Further aspects of this type of tag are described in the above-mentioned U.S. patent application Ser. No. 10/029,473.

To determine the position of tag 54, electric fields are applied to the area of the patient's body containing the tag by a number of field generators in different, known positions and/or orientations. Preferably, each of the field generators has its own, distinct operating frequency. Control circuitry 58 measures the currents flowing in sensor coil 56 at the different field frequencies and encodes the measurements in a high-frequency signal transmitted via antenna 22. Alternatively or additionally, the different field generators are time-multiplexed, each operating during its own preassigned time slots.

In the embodiment pictured in FIG. 5, circuitry 58 comprises a voltage-to-frequency (V/F) converter 62, which generates a RF signal whose frequency is proportional to the voltage produced by the sensor coil current flowing across a load. Preferably, the RF signal produced by circuitry 58 has a carrier frequency in the 50-150 MHz range. The RF signal produced in this manner is modulated with a number of different frequency modulation (FM) components that vary over time at the respective frequencies of the fields generated by the field generators. The magnitude of the modulation is proportional to the current components at the different frequencies. A receiver outside the patient's body demodulates the RF signal to determine the magnitudes of the current components and thereby to calculate the coordinates of tag 54.

Alternatively, circuitry 58 may comprise a sampling circuit and analog/digital (A/D) converter (not shown in the figures), which digitizes the amplitude of the current flowing in sensor coil 56. In this case, circuitry 58 generates a digitally-modulated signal, and RF-modulates the signal for transmission by antenna 22. Any suitable method of digital encoding and modulation may be used for this purpose. Other methods of signal processing and modulation will be apparent to those skilled in the art.

Figure 6:
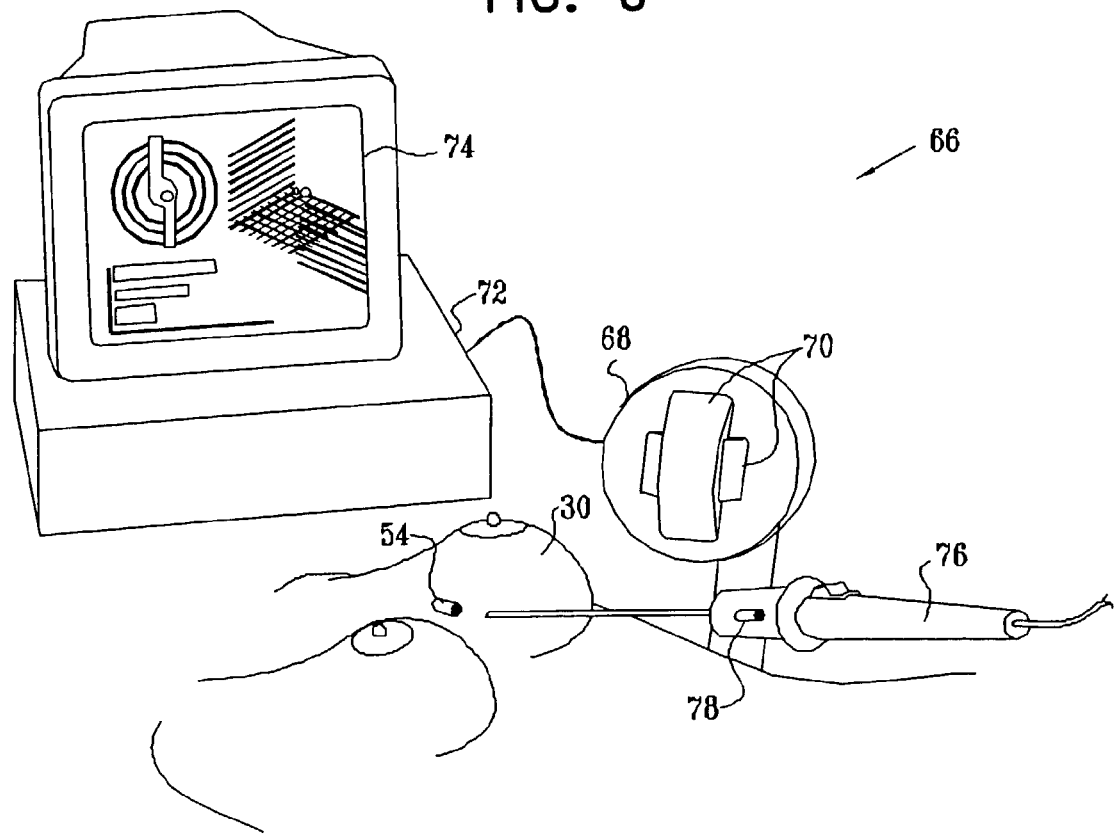
FIG. 6 is a schematic, pictorial illustration of a system for guiding a surgical probe to the location of a passive tag in the breast of a subject, in accordance with a preferred embodiment of the present invention.

FIG. 6 is a schematic, pictorial illustration of a system 66 for guiding a surgical tool 76 to the location of tag 54 in breast 30, in accordance with a preferred embodiment of the present invention. A power coil 68 generates a high-frequency RF field, preferably in the 2-10 MHz range. This field causes a current to flow in antenna 22, which is rectified by circuitry 58 and used to power its internal circuits. Meanwhile, field generator coils 70 produce electromagnetic fields, preferably in the 1-3 kHz range, which cause currents to flow in sensor coil (or coils) 56. These currents have frequency components at the same frequencies as the driving currents flowing through the generator coils. The current components are proportional to the strengths of the components of the respective magnetic fields produced by the generator coils in a direction parallel to the sensor coil axis. Thus, the amplitudes of the currents indicate the position and orientation of coil 56 relative to fixed generator coils 70.

Circuitry 58 encodes the current amplitudes from coil 56 into a high-frequency signal, which is transmitted by antenna 22. Alternatively, tag 54 may comprise separate antennas for receiving RF power and for transmitting signals, as described, for example, in the above-mentioned U.S. Pat. No. 6,239,724. The encoded signal is received by coil 68 or by another receiving antenna, and is conveyed to a processing unit 72. Typically, processing unit 72 comprises a general-purpose computer, with suitable input circuits and software for processing the position signals received over the air from tag 54. The processing unit computes position and, optionally, orientation coordinates of tag 54, and then shows the tag coordinates on a display 74.

Surgical tool 76 also comprises a position sensor 78, comprising one or more coils similar in form and function to coils 56 in tag 54. The fields produced by field generator coils 70 also cause currents to flow in sensor 78, in response to the position and orientation of tool 76 relative to coils 70. The current signals thus produced are also conveyed to processing unit 72, either over the air, as in the case of tag 54, or via wire. If sensor 78 transmits the signals over the air, it preferably uses a different carrier frequency from that of tag 54 so that the signals can be easily distinguished one from another.

Based on the signals from tag 54 and from sensor 78, processing unit 72 computes the position and orientation of tool 76 relative to the location of the tag in breast 30. A pointer and/or cursor is shown on display 74 to indicate to the surgeon whether the tool is aimed properly towards its target. Various methods of coordinate display may be used for this purpose, such as a three-dimensional grid mesh, a two-dimensional grid, a two- or-three dimensional polar representation, numerical coordinate readout, or other methods known in the art. Optionally, the positions of the tag and tool are registered, using their measured positions and orientations, with an image of breast 30, such as an X-ray, CT or ultrasound image. The image of the breast is shown on display 74, and icons corresponding to the positions of the tag and the tool are superimposed on the image. Further methods of display that are useful in image-guided surgery are described in the above-mentioned U.S. Pat. No. 6,332,098.

Figure 7:
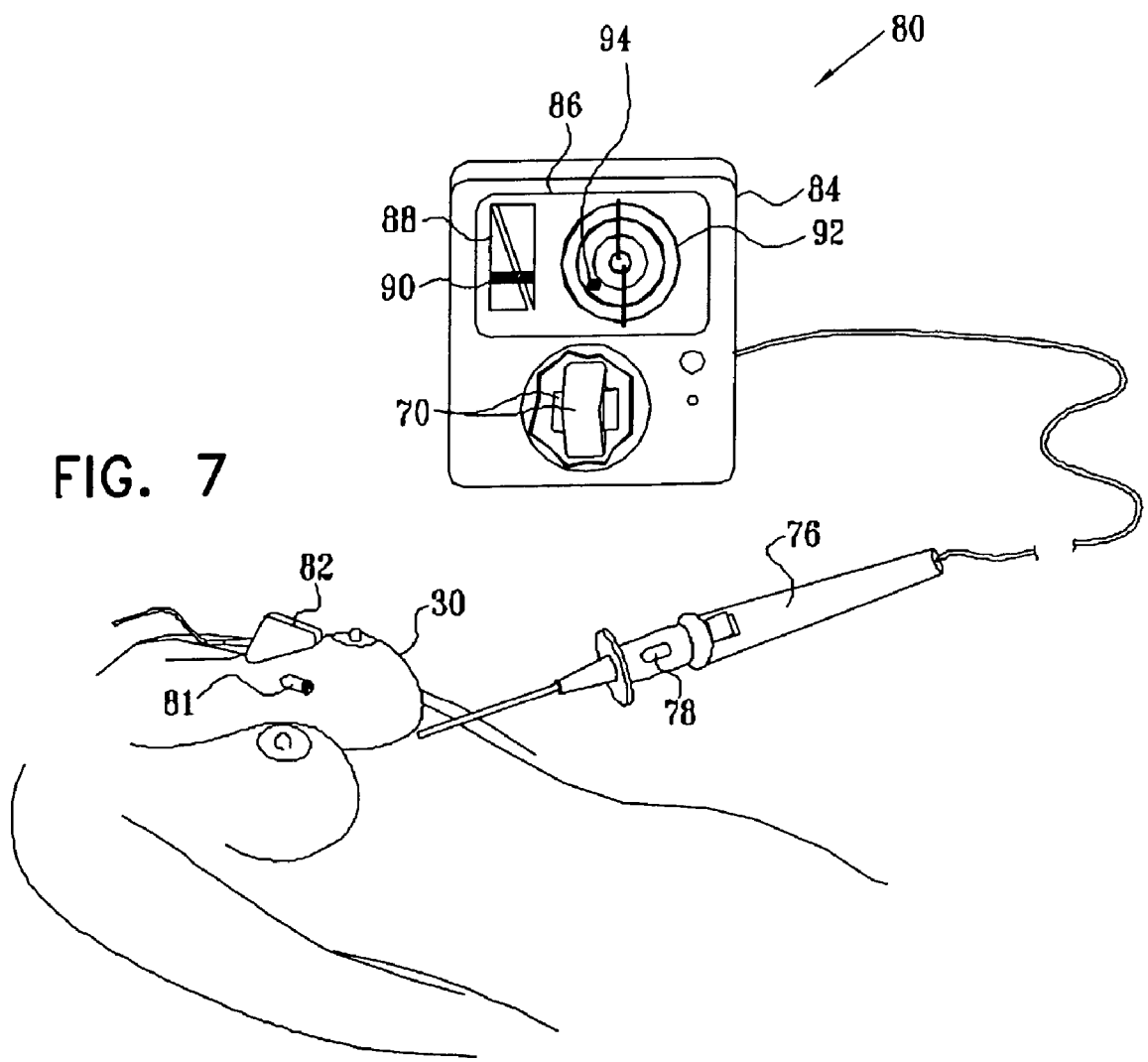
FIG. 7 is a schematic, pictorial illustration of a system for guiding a surgical probe to the location of a passive tag in the breast of a subject, in accordance with another preferred embodiment of the present invention.

FIG. 7 is a schematic, pictorial illustration of a system 80 for guiding surgical tool 76 to the location of a tag 81 in breast 30, in accordance with another preferred embodiment of the present invention. In this embodiment, a tag 81 receives its operating power not from an electromagnetic field (such as that of coil 68), but from acoustic energy generated by an ultrasound transmitter 82. A tag of this sort is shown, for example, in the above-mentioned U.S. patent application Ser. No. 10/029,595. The acoustic energy generated by transmitter 82 excites a miniature transducer, such as a piezoelectric crystal, in tag 81, to generate electrical energy. The electrical energy causes a current to flow in one or more coils in tag 81, such as coil 56 described above. The currents in the coils in tag 81 generate electromagnetic fields outside breast 30, which are in this case received by coils 70 (now acting as field receivers, rather than field generators). The amplitudes of the currents flowing in coils 70 at the frequency of the applied acoustic energy are measured to determine the position of tag 81.

Alternatively, tag 81 may be similar in operation to tag 54, in that sensor coil or coils 56 in the tag receive a field generated by coils 70, and then circuitry in the tag transmits a signal indicating the amplitudes of the current components in coils 56. In the embodiment of FIG. 7, however, the circuitry in the tag receives power not from coil 68, but rather by rectifying the electrical energy generated by the piezoelectric crystal (or other transducer) in tag 81 in response to the acoustic energy applied by transmitter 82. The tag may transmit its signal in pulses, rather than continuously, and a capacitor may be used to store energy in tag 81 in the intervals between the pulses, so that the transmitted signal is powerful enough to be received outside the body with good signal/noise ratio.

As in the preceding embodiment, sensor 78 is used to determine the position and orientation of tool 76. Sensor 78 may either receive the fields generated by coils 70, as described above, or it may be driven to generate fields, which are received by coils 70.

The position signals generated by tag 81 and sensor 78 are received and processed by a combined location pad and display unit 84. This unit takes the place of the separate processing unit 72, coils 70 and display 74 used in the preceding embodiment. Unit 84 is preferably held by a stable, movable mount (not shown), enabling the surgeon to place the unit in proximity to breast 30 and in a position in which a display 86 on the unit can be viewed conveniently. Field generator coils 70 are built into unit 84, so that the positions of tag 81 and tool 76 are determined relative to the unit. (Coils 70 are seen in the figure in cutaway view, but ordinarily would be contained inside the case of the unit, protected by a non-conductive cover.) Since it is not the absolute positions of tag 81 and tool 76 that are of concern, but rather their relative positions and orientations, the surgeon may move unit 84 during the surgery as required, in order to ensure that the signals from tag 81 and sensor 78 are sufficiently strong, that display 86 is easily visible, and that the unit itself does not interfere with the surgeon's work.

Display 86 preferably comprises a distance guide 88 and an orientation target 92. A mark 90 on distance guide 88 indicates how far the tip of tool 76 is from the location of tag 81. A cursor 94 on target 92 indicates the orientation of tool 76 relative to the axis required to reach the location of tag 81. When the cursor is centered on the target, it means that tool 76 is pointing directly toward tag 81. Display 38 (FIG. 2) preferably works on a similar principle.

Figure 8:
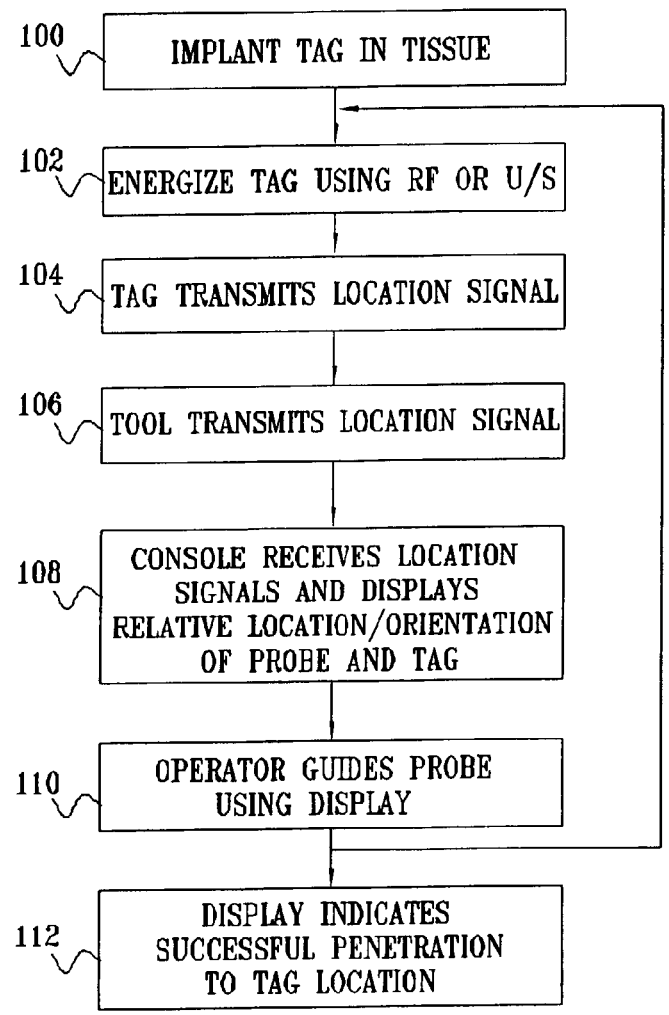
FIG. 8 is a flow chart that schematically illustrates a method for carrying out an invasive medical procedure on body tissue using a tag implanted in the tissue, in accordance with a preferred embodiment of the present invention.

FIG. 8 is a flow chart that schematically illustrates a method for performing a surgical procedure using system 80, including tag 81 and combined location pad and display unit 84, in accordance with a preferred embodiment of the present invention. A similar procedure may be carried out, mutatis mutandis, using the elements of system 66, shown in FIG. 6. As described above with reference to FIG. 3, the procedure begins with implantation of the appropriate tag at the target location in breast 30, at an implant step 100. The tag is then energized by applying transmitter 82 to the breast, and driving the transmitter to generate acoustic energy, at an energizing step 102. Alternatively, if tag 54 is used, coil 68 is used to energize the tag with RF power.

Energizing the tag causes it to transmit a location signal to unit 84, at a tag transmission step 104. At the same time, or in alternation with the tag transmission, sensor 78 conveys a location signal to unit 84, as well, at a tool transmission step 106. Unit 84 (or processing unit 72, in the embodiment of FIG. 6) receives the location signals and determines the relative coordinates of tool 76 and tag 81, at a coordinate determination step 108. Based on this determination, the location and orientation of the tool relative to the tag are shown on display 86 in the manner described above.

The surgeon uses the information presented by display 86 to guide the distal end of tool 76 to the location of tag 81, at a probe guidance step 110. In typical operation, the surgeon holds the tool at a selected starting position and aims it toward tag 81, using target 92. The surgeon then advances the tool into breast 30, keeping cursor 94 centered on target 92. Steps 102 through 110 are repeated continually until mark 90 indicates that the tool has reached the location of tag 81, at a success step 112. The biopsy or other desired procedure can then be performed.

Figure 9:
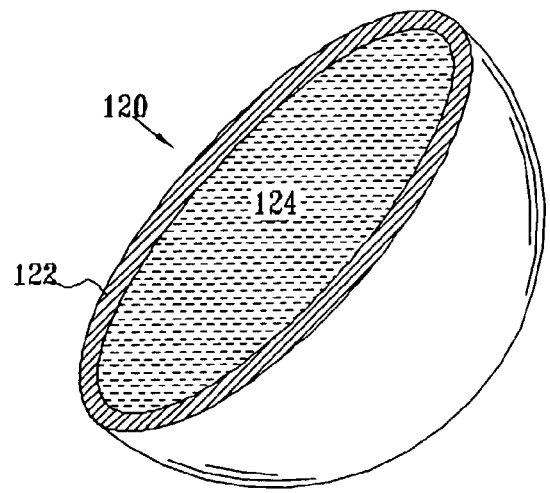
FIG. 9 is a schematic, pictorial illustration showing a cutaway view of an ultrasonic reflecting tag, in accordance with a preferred embodiment of the present invention.

FIG. 9 is a schematic, pictorial, partly-cutaway illustration of an ultrasonic reflecting tag 120, in accordance with another preferred embodiment of the present invention. Various tags of this sort, which are applicable to the purposes of the present invention, are shown and described in the above-mentioned U.S. patent application Ser. No. 10/029,595. Tag 120 in the present embodiment has the form of a spherical bubble, comprising a shell 122 that is struck by ultrasound waves generated by acoustic transducers outside the patient's body. The incident ultrasound waves induce the tag to resonate and to emit a detectable ultrasound echo. If shell 122 is spherical (as shown), then the emitted echo is generally isotropic, and triangulation of the echo can yield the location of the target in the body.

Preferably, shell 122 contains a medium 124, and the shell and medium are configured so that tag 120 has a nonlinear vibrational response to incident ultrasonic radiation. Ultrasound waves having a frequency f1, emitted by the acoustic generators outside the patient's body, strike the shell, imparting energy to the shell and/or the contained medium. The shell then emits ultrasound waves at its resonant frequency f2, which is different from f1. The resonant frequency is determined by parameters such as the shell radius, Young modulus and thickness, as is known in the art. Preferably, to generate strong echoes, the design parameters of tag 120 and the excitation frequency f1 are chosen so that f2 is a multiple of f1.

Figure 10:
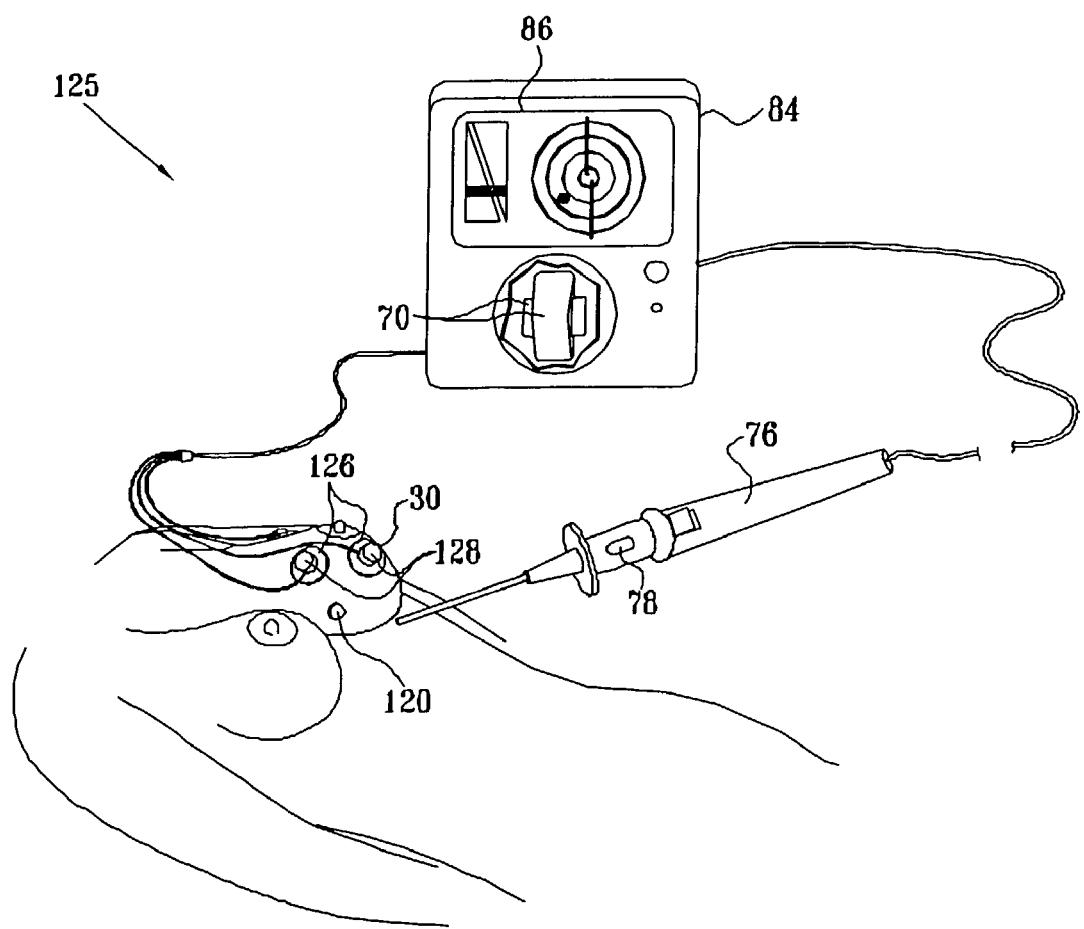
FIG. 10 is a schematic, pictorial illustration of a system for guiding a surgical probe to the location of a passive tag in the breast of a subject, in accordance with still another preferred embodiment of the present invention.

FIG. 10 is a schematic, pictorial illustration showing a system 125 for guiding surgical tool 76 to the location of tag 120 in breast 30, in accordance with a preferred embodiment of the present invention. This embodiment also uses the combined location pad and display unit 84 described above. Multiple ultrasonic transducers 126 are applied to breast 30. Each transducer in turn is driven to generate a pulse of ultrasonic energy at frequency f1, and then to detect the echo signal returned by tag 120 at frequency f2. Alternatively or additionally, all the transducers may detect the echo returned due to the ultrasonic pulses generated by a single one of the transducers. The time delay between generation of the ultrasonic pulse and receipt of the echo indicates the distance from each of transducers 126 to tag 120. Alternatively or additionally, the power of the echo signal received by each of transducers 126 may be used to determine the distances.

To determine the actual location of tag 120 in breast 30, however, it is necessary to know the locations of transducers 126. For this purpose, a sensor coil 128 is attached to each of the transducers. Energizing field generator coils 70 in unit 84 causes currents to flow in sensor coils 128. The amplitudes of these currents, as noted above, depend on the locations and orientations of the sensor coils relative to the field generator coils. Unit 84 analyzes the currents flowing in sensor coils 128 in order to determine the position coordinates of transducers 126. Based on these coordinates, along with the distances measured by ultrasound reflection from each of transducers 126 to tag 120, unit 84 is able to determine the exact location of the tag in a fixed, external frame of reference.

The location and orientation coordinates of tool 76 relative to unit 84 are determined using sensor 78, as described above, so that the distance and direction from the tool to tag 120 can also be calculated and displayed.

It will be observed that system 125 uses two sets of position measurements to find the location of tag 120: location of transducers 126 relative to unit 84, and location of tag 120 relative to the transducers. This added level of complication is not present in the embodiments described earlier. On the other hand, by comparison with tags 20, 54 and 81, tag 120 is extremely simply and inexpensive to fabricate and can be made very small if desired. Typically, tag 120 has a diameter less than 2 mm.

Figure 11:
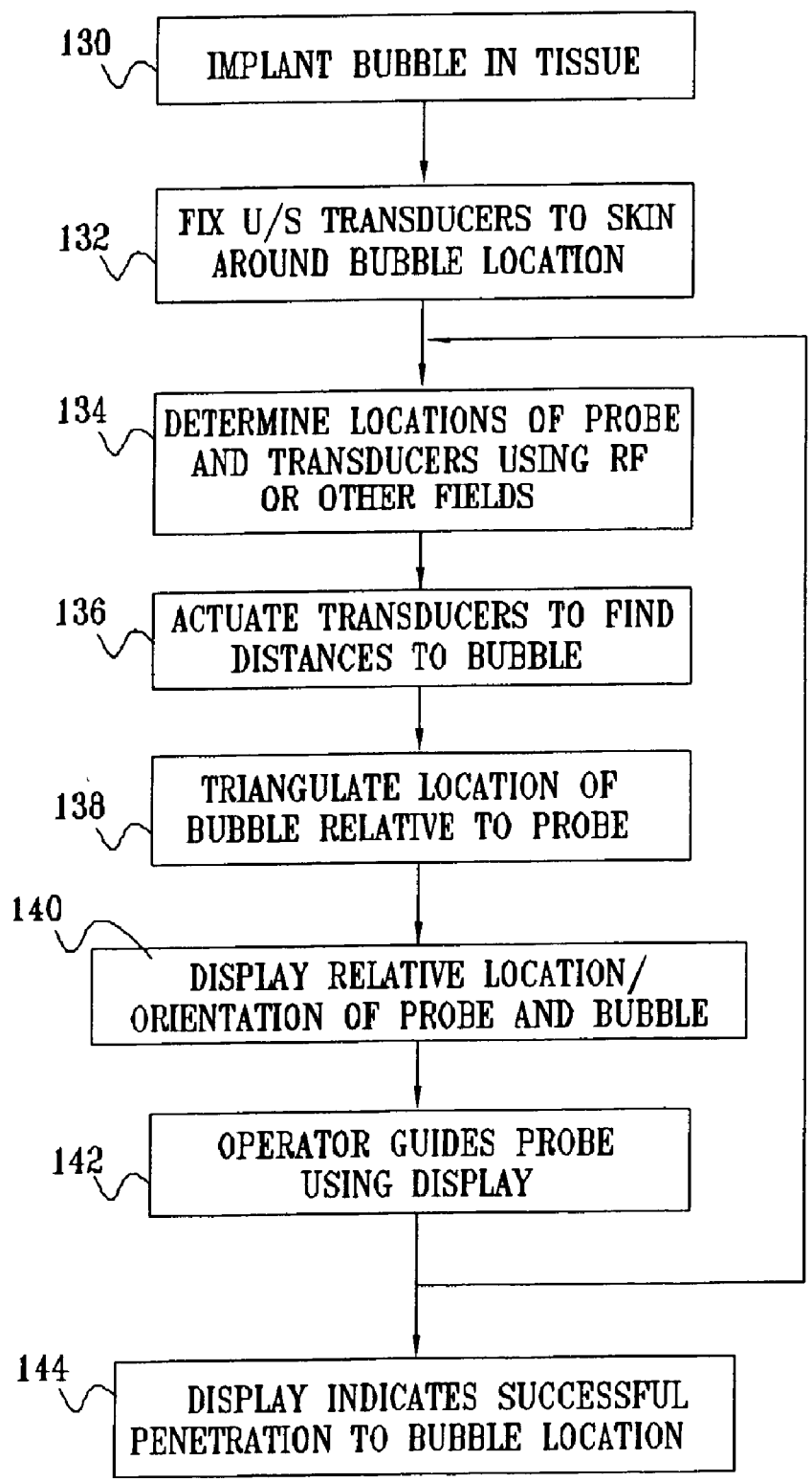
FIG. 11 is a flow chart that schematically illustrates a method for carrying out an invasive medical procedure on body tissue using a tag implanted in the tissue, in accordance with a preferred embodiment of the present invention.

FIG. 11 is a flow chart that schematically illustrates a method for performing a surgical procedure using system 125, including tag 120, in accordance with a preferred embodiment of the present invention. In this embodiment, too, the procedure starts with implantation of tag 120 by a radiologist at the site of a suspected lesion in breast 30, at an implant step 130. Preferably, for this purpose, the material of shell 122 is selected so as to be clearly visible using standard imaging techniques. Then, in preparation for surgery, transducers 126 are fixed to the skin of breast 30 around the location of tag 120, at a transducer fixation step 132.

In order to find the relative positions and orientations of tool 76 and transducers 126, field generator coils 70 are actuated, and the currents flowing in sensor 78 and sensor coils 128 are measured, at a RF location step 134. Alternatively, other position sensing techniques may be used for this purpose. For example, optical sensing techniques may be used to find the coordinates of tool 76 and of transducers 126 at step 134, since both tool 76 and transducers 126 are outside the patient's body. Ultrasonic position sensing techniques may likewise be used.

Transducers 126 are actuated, and the echoes received by the transducers from tag 120 are measured, at an echo measurement step 136. The echoes are used to determine the distance from each of transducers 126 to tag 120, as described above. (The order of steps 134 and 136 may alternatively be reversed.) Unit 84 then performs the necessary geometrical calculations and transformations to find the position and orientation of tool 76 relative to tag 120, at a triangulation step 138. The distance of the tool from the tag and the orientation of the tool relative to the direct approach axis to the tag are shown on display 86, at a display step 140, as described above.

The surgeon uses the information presented by display 86 to guide the distal end of tool 76 to the location of tag 120, at a probe guidance step 142. The surgeon advances the tool into breast 30, keeping cursor 94 centered on target 92, as described above. Steps 134 through 142 are repeated continually until mark 90 indicates that the tool has reached the location of tag 81, at a success step 144. The biopsy or other desired procedure can then be performed.

Although the preferred embodiments described above all relate to breast surgery, and particularly to breast biopsy, the devices and methods used in these embodiments may also be adapted to other procedures and to treatment of other body organs. For example, tags such as those described above may be implanted in body tissues to be treated by high-intensity focused radiation. Such techniques are typically used for ablation of tumors and other lesions inside the body. In therapeutic applications of this sort, the radiologist would implant the tag at the location to be treated, and the radiation sources to be used for the treatment would then be aimed at the tag location. Referring again to FIG. 10, for instance, if transducers 126 were of a type suitable to be used in high-intensity focused ultrasound (HIFU) treatment, they could be oriented and aimed toward the location of tag 120 using the position signals and display generated by unit 84.

Figure 12:
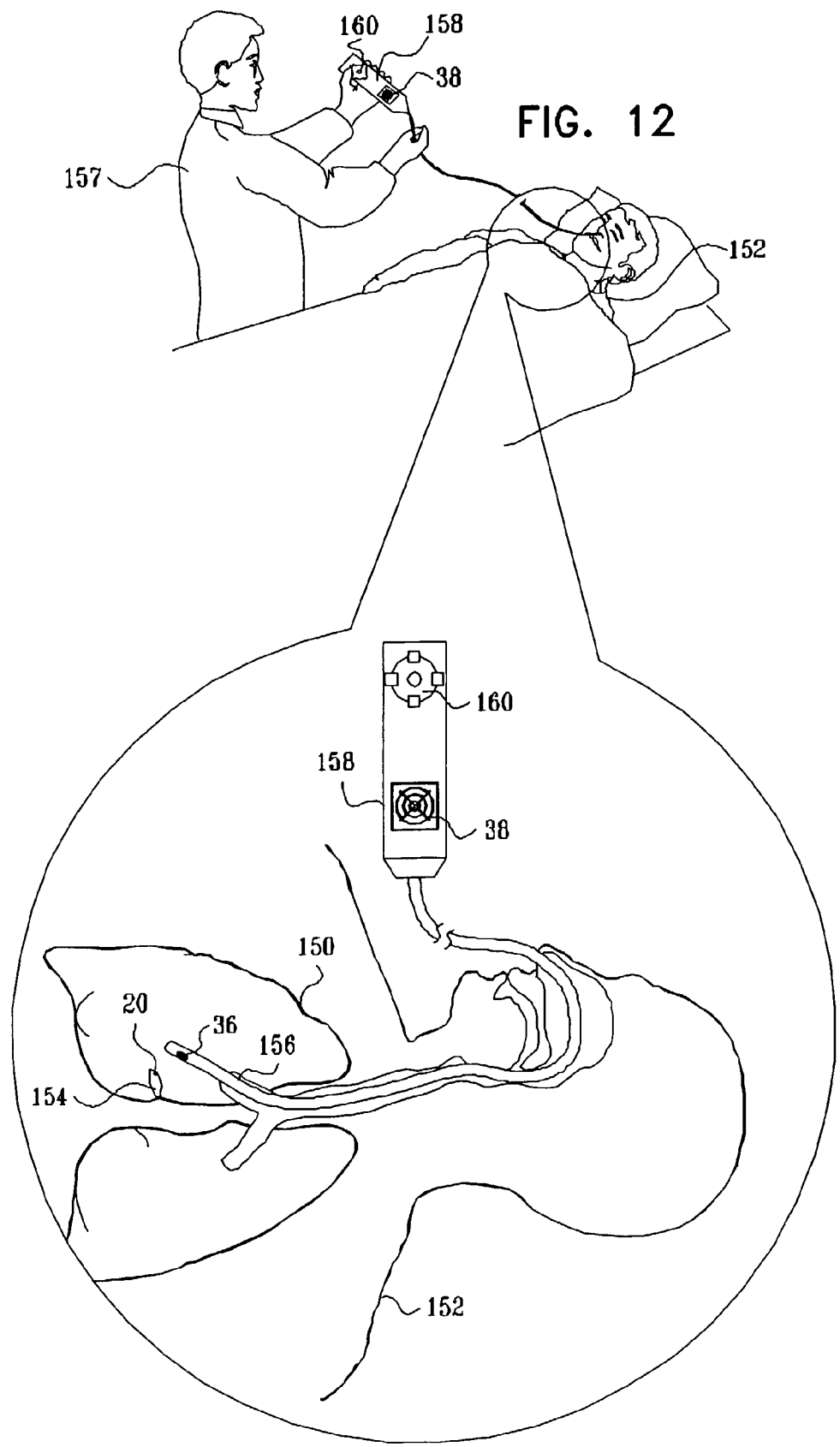
FIG. 12 is a schematic, pictorial illustration showing an endoscope that is guided to the location of a passive tag in the lung of a subject using a display on the endoscope, in accordance with a preferred embodiment of the present invention.

FIG. 12 is a schematic, pictorial illustration showing the use of tag 20 in a bronchoscopy procedure, in accordance with a preferred embodiment of the present invention. Tag 20 is fixed to a suspicious nodule 154, which was discovered during an imaging procedure performed in a lung 150 of a patient 152. A bronchoscope 156 is used to inspect and, possibly, to biopsy nodule 154. It is also desirable to be able to return easily to the same nodule location for follow-up in subsequent bronchoscopic examinations. A physician 157 operates bronchoscope 156 by grasping and manipulating a handle 158. Bronchoscope comprises elements similar to tool 32 shown in FIG. 2: antenna assembly 36 (suitably adapted and miniaturized) at the distal end of the bronchoscope, and display 38 on handle 158. While viewing the display, physician 157 turns a steering knob 160 and advances the bronchoscope into lung 150 until it reaches the location of nodule 154.

Although this embodiment is based on tag 20, as shown in FIG. 1, the other RF-based tags described above (such as tag 54 shown in FIG. 4) may also be used for this purpose. Tags based on the use of ultrasound, on the other hand, are typically less satisfactory for pulmonary applications.

FIG. 13 is a schematic, pictorial illustration showing the use of tag 120 in a colonoscopy procedure, in accordance with a preferred embodiment of the present invention. In this example, tag 120 is fixed to a polyp 164 that was discovered in a colon 162 of a patient. Ultrasound transducers 126 (as shown in FIG. 10, but not in this figure) are fixed to the patient's abdomen, to enable the location of tag 120 to be determined, in the manner described above. A colonoscope 160 is advanced through colon 162, and its position is tracked by means of sensor 78. As the distal end of the colonoscope approaches the location of tag 120, unit 84 displays the distance and direction from the colonoscope to the tag. Optionally, an icon indicating the position of tag 120 is superimposed on a video image of the interior of colon 162 that is formed by an image sensor in the colonoscope and displayed on a suitable video display.

Although the preferred embodiments described above are directed to certain specific medical and surgical procedures in particular body organs, other areas of application of the tags, ancillary equipment and methods of the present invention will be apparent to those skilled in the art. The principles of the present invention may similarly be applied to other types of surgery, including particularly minimally-invasive surgery, as well as endoscopic and non-invasive treatment and diagnostic modalities.

It will thus be appreciated that the preferred embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for performing a medical procedure on a tissue within a body of a subject, comprising:
a wireless tag configured to be fixed to the tissue and adapted to emit radiation, thereby causing first signals to be generated indicative of location and orientation coordinates of the tag in the body;
an invasive medical tool, comprising:
a probe, which is adapted to penetrate into the body so as to reach the tissue;
a handle, fixed proximally to the probe, and adapted to be manipulated by an operator of the tool; and
a display, mounted on the handle, and adapted to present a visual indication to the operator of an orientation of the probe relative to the tag based on the location and orientation coordinates; and
a processing unit, coupled to process the first signals so as to determine the location and orientation coordinates of the tag relative to the probe, and to drive the display responsive to the location and orientation coordinates.

2. Apparatus according to claim 1, wherein the invasive medical tool further comprises a receiver, which is adapted to receive the radiation emitted by the wireless tag, and to generate the first signals responsive thereto for processing by the processing unit.

3. Apparatus according to claim 2, wherein the radiation emitted by the tag comprises radio-frequency (RF) electromagnetic radiation.

4. Apparatus according to claim 1, wherein the invasive medical tool further comprises a tool position sensor, which is adapted to generate second signals indicative of the location and orientation coordinates of the probe, and wherein the processing unit is coupled to process the second signals together with the first signals so as to determine the location and orientation coordinates of the tag relative to the probe.

5. Apparatus according to claim 4, and comprising one or more field generators, which are fixed in the external frame of reference and which are adapted to generate electromagnetic fields in a vicinity of the tissue, and wherein the wireless tag and the tool position sensor comprise field sensors, in which electrical currents flow responsive to the electromagnetic fields, and wherein the first and second signals are indicative of the electrical currents flowing in the field sensors.

6. Apparatus according to claim 1, wherein the radiation emitted by the tag comprises radio-frequency (RF) electromagnetic radiation.

7. Apparatus according to claim 6, and comprising one or more acoustic transmitters, which are adapted to transmit acoustic energy into the body in a vicinity of the tissue, and wherein the tag is adapted to receive and use the acoustic energy in generating the electromagnetic radiation.

8. Apparatus according to claim 1, wherein the radiation emitted by the tag comprises acoustic radiation.

9. Apparatus according to claim 1, wherein the display is adapted to present a further visual indication of a distance from the probe to the tag.

10. Apparatus according to claim 1, wherein the invasive medical tool is adapted to perform a surgical procedure on the tissue.

11. Apparatus according to claim 1, wherein the invasive tool comprises an endoscope.

12. Apparatus according to claim 1, wherein the location and orientation coordinates are six-dimensional location and orientation coordinates.

13. A method for performing a medical procedure on a tissue within a body of a subject, comprising:
fixing a wireless tag to the tissue;
actuating the tag to emit radiation, thereby causing first signals to be generated indicative of location and orientation coordinates of the tag in the body;
introducing an invasive medical tool into the body by manipulating a handle of the tool;
processing the first signals so as to determine the location and orientation coordinates of the tag relative to the tool;
responsive to location and orientation the coordinates, displaying a visual indication on the handle of the tool of an orientation of the tool relative to the tag; and advancing the tool into the body to the tissue by manipulating the handle while observing the visual indication so that the tool reaches the tissue.

14. A method according to claim 13, wherein processing the first signals comprises receiving the radiation emitted by the wireless tag using a receiver in the medical tool, and generating the first signals responsive to the received radiation.

15. A method according to claim 14, wherein receiving the radiation emitted by the tag comprises receiving radio-frequency (RF) electromagnetic radiation.

16. A method according to claim 13, and comprising receiving second signals generated by a tool position sensor coupled to the invasive medical tool, indicative of the location and orientation coordinates of the tool, and wherein processing the first signals comprises processing the second signals together with the first signals so as to determine the location and orientation coordinates of the tag relative to the probe.

17. A method according to claim 16, wherein actuating the tag comprises generating electromagnetic fields in a vicinity of the tissue, and wherein the wireless tag and the tool position sensor comprise field sensors, in which electrical currents flow responsive to the electromagnetic fields, and wherein the first and second signals are indicative of the electrical currents flowing in the field sensors.

18. A method according to claim 12, wherein actuating the tag comprises actuating the tag to emit radio-frequency (RF) electromagnetic radiation.

19. A method according to claim 18, wherein actuating the tag to emit RF electromagnetic radiation comprises transmitting acoustic energy into the body in a vicinity of the tissue, wherein the tag receives and uses the acoustic energy in generating the electromagnetic radiation.

20. A method according to claim 13, wherein actuating the tag comprises actuating the tag to emit acoustic radiation.

21. A method according to claim 13, and comprising displaying a further visual indication of a distance from the probe to the tag.

22. A method according to claim 13, wherein advancing the tool into the body comprises performing a surgical procedure on the tissue.

23. A method according to claim 1, wherein advancing the tool into the body comprises performing an endoscopic procedure on the tissue.

24. A method according to claim 13, further comprising determining six-dimensional location and orientation coordinates of the tag relative to the tool.

* * * * *